(12) United States Patent
Kipke et al.

(10) Patent No.: US 8,972,026 B2
(45) Date of Patent: Mar. 3, 2015

(54) IMPLANTABLE NEURAL INTERFACE DEVICE WITH A CONNECTOR HAVING A SLITTED DEFORMABLE SECTION

(71) Applicant: NeuroNexus Technologies, Inc., Clarence, NY (US)

(72) Inventors: Daryl R. Kipke, Dexter, MI (US); Jamille Farraye Hetke, Brooklyn, MI (US); Rio J. Vetter, Ypsilanti, MI (US); John P. Seymour, Ann Arbor, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 115 days.

(21) Appl. No.: 13/741,864

(22) Filed: Jan. 15, 2013

(65) Prior Publication Data

US 2013/0184795 A1  Jul. 18, 2013

Related U.S. Application Data

(60) Provisional application No. 61/587,606, filed on Jan. 17, 2012.

(51) Int. Cl.
| | |
|---|---|
| *A61N 1/00* | (2006.01) |
| *A61N 1/05* | (2006.01) |
| *A61N 1/36* | (2006.01) |
| *A61B 5/0478* | (2006.01) |
| *A61B 5/04* | (2006.01) |
| *A61B 5/00* | (2006.01) |

(52) U.S. Cl.
CPC .............. *A61N 1/0551* (2013.01); *A61N 1/05* (2013.01); *A61B 5/04001* (2013.01); *A61N 1/0529* (2013.01); *A61N 1/0539* (2013.01); *A61N 1/36* (2013.01); *A61B 5/686* (2013.01); *A61B 5/6868* (2013.01); *A61B 5/0478* (2013.01); *A61B 2562/187* (2013.01)
USPC .......................................... 607/116; 600/373

(58) Field of Classification Search
CPC ... A61N 1/05–1/0558; A61N 1/3605–1/36064
USPC ........................... 600/373–391; 607/115–156
See application file for complete search history.

(56) References Cited

U.S. PATENT DOCUMENTS

| 7,363,082 B2 | 4/2008 | Ransbury et al. |
| 7,548,775 B2 | 6/2009 | Kipke et al. |

(Continued)

FOREIGN PATENT DOCUMENTS

WO    2011157714    12/2011

OTHER PUBLICATIONS

European Search Report dated Mar. 25, 2013 for Application No. 13151575.1.

*Primary Examiner* — Scott Getzow
(74) *Attorney, Agent, or Firm* — Michael F. Scalise (57) ABSTRACT

An improved deformable carrier or connector for an implantable neural interface device is described. The neural interface device comprises a carrier supporting at least one electrode array. The carrier comprises a tubular sidewall extending from a proximal carrier portion to a distal carrier portion. At least one deformable segment is provided in the carrier sidewall. The deformable segment is more pliable than the remainder of the carrier sidewall to preferably move in response to forces imparted on the carrier and the electrode array by the shifting forces in body tissue. The deformable segment takes the form of a thinned sidewall segment or a slitted wall segment.

20 Claims, 8 Drawing Sheets

(56) References Cited

U.S. PATENT DOCUMENTS

| | | |
|---|---|---|
| 8,116,883 B2 | 2/2012 | Williams et al. |
| 8,224,417 B2 | 7/2012 | Vetter |
| 2002/0198522 A1* | 12/2002 | Kordis .......................... 606/41 |
| 2007/0213795 A1 | 9/2007 | Bradley et al. |
| 2007/0265673 A1 | 11/2007 | Ransbury et al. |
| 2008/0039917 A1 | 2/2008 | Cross et al. |
| 2008/0132933 A1 | 6/2008 | Gerber |
| 2009/0240314 A1 | 9/2009 | Kong et al. |
| 2009/0299166 A1 | 12/2009 | Nishida et al. |
| 2011/0093052 A1 | 4/2011 | Anderson et al. |

* cited by examiner

IMPLANTABLE NEURAL INTERFACE DEVICE WITH A CONNECTOR HAVING A SLITTED DEFORMABLE SECTION

CROSS-REFERENCE TO RELATED APPLICATION

This application claims priority from U.S. Provisional Patent Application Ser. No. 61/587,606, filed on Jan. 17, 2012.

FIELD OF THE INVENTION

This invention relates generally to the implantable medical devices and, more specifically, to an improved implantable neural interface device with a deformable carrier or connector.

BACKGROUND OF THE INVENTION

Conventional carriers or connectors for neural interface devices, such as those with electrode arrays for deep brain and central nervous system applications, have a tendency to "drift" after implantation in targeted tissue. This is due, in part, to the mechanical mismatch between the relatively stiff carrier for the neural interface device and the target body tissue and, in part, to tissue regrowth around the neural interface device. Any relative movement between the neural interface device and body tissue can result in the electrode array moving away from the targeted tissue. Thus, there is a need in the implantable medical device field for an improved carrier or connector for an implantable neural interface device. The present invention provides such an improved deformable carrier or connector for an implantable neural interface device.

DESCRIPTION OF THE PREFERRED EMBODIMENTS

Turning now to the drawings, FIGS. 1 and 1A to 1C illustrate a preferred embodiment of an implantable neural interface device 10 according to the present invention. The neural interface device 10 is implantable into a wide variety of body tissue including the brain, spinal cord, peripheral nerve, muscle, and/or any suitable neural tissue and comprises a carrier 12 supporting at least one electrode array 14.

The electrode array 14 may be made from a thin-film polymer substrate such that there is a high density of electrode sites at a first end of the array (e.g., the distal end) and bonding regions at a second end of the array (e.g., the proximal end). The polymer substrate is preferably parylene, polyimide, silicone or a suitable combination of organic and inorganic dielectrics, but may additionally and/or alternatively be made of any suitable material. The substrate can also include a dielectric layer comprised of silicon nitride, silicon dioxide, silicon carbide, and mixtures thereof.

The carrier 12 is preferably of silicone or polyurethane and comprises a tubular sidewall 16 having a length extending from a proximal carrier portion 12A to a distal carrier portion 12B. The distal carrier portion 12B has a step 12C transition to a thin-walled distal. end 12D. The step 12C has a height that substantially matches the thickness of the thin film substrate comprising the electrode array 14. That way, the electrode array 14 is wrapped and otherwise supported at least part way around the circumference of the distal carrier end 12D to provide a smooth transition to the distal carrier portion 12B. To facilitate adhesion between the carrier 12 and electrode array 14, small non-homogenous perforations may be micromachined into the thin-film substrate to allow for the material of the carrier 12 to form a robust anchor with the electrode array 14.

At least one deformable segment 18 is provided along the length of the carrier 12 intermediate a first carrier sidewall portion 16A and a second carrier sidewall portion 16B. As will be described in greater detail hereinafter, the deformable segment 18 is a portion or location along the carrier 12 that is compressible, tensile, articulatable, and/or rotatable along an axis thereof, such as a longitudinal axis of the carrier. Compression or extension of the deformable segment 18 results in translation of the carrier sidewall portions 16A, 16B relative to one another along an axis of insertion (e.g., longitudinal axis along the carrier). However, the deformable segment 18 may additionally and/or alternatively bend or rotate or deform in any other suitable manner along any suitable axis. For instance, the deformable segment 18 may bend or curve to enable the sidewall portions 16A, 16B to become axially misaligned or curved along the length of the carrier 12. In an alternative embodiment, the entire length of the carrier 12 is substantially equivalent to a deformable segment 18 such that the carrier is adapted to deform in compression, extension, and/or any other suitable manner.

An electrical conductor 20 extends from the proximal carrier portion 12A to the distal carrier portion 12B where the conductor electrically connects to at least one electrode site 22 of the electrode array 14 supported by the distal carrier end 12D. As will be described in greater detail hereinafter, the electrode site 22 is exemplary of a stimulation electrode configured for electrical stimulation of body tissue or a recording electrode for recording of physiological data from body tissue. In that respect, the novel carrier 12 facilitates insertion or implantation of the electrode array 14 into body tissue and, once implanted, helps mitigate or eliminate drift (movement) of the implanted electrode array 14 within the tissue.

The conductor 20 preferably has coiled or otherwise stretchable or deformable sections 20A that coincide with the deformable segments 18 in the carrier 12 of the neural interface device 10. The conductor 20 is preferably a thin-film structure containing multiple individually conductive traces, but may be a wire or any suitable conductive material. The conductor 20 may be wound around the external surface of the carrier 12, wound within a wall of the carrier, or wound around an internal surface of the carrier. The coiling or winding density is preferably selectively varied along the length of the carrier 12 to modulate the flexibility of the conductor 20. In a preferred embodiment, the conductor 20 include at least one section of lower coiling density corresponding to or aligned with a deformable segment 18 and at least one section of higher coiling density corresponding to or aligned with one of the carrier sidewall section 16A, 16B. In that manner, the carrier 12 and coiled conductor 20 may be deformable in tandem in compression, tension or extension, articulation, rotation and/or any suitable manner.

Figure 1:
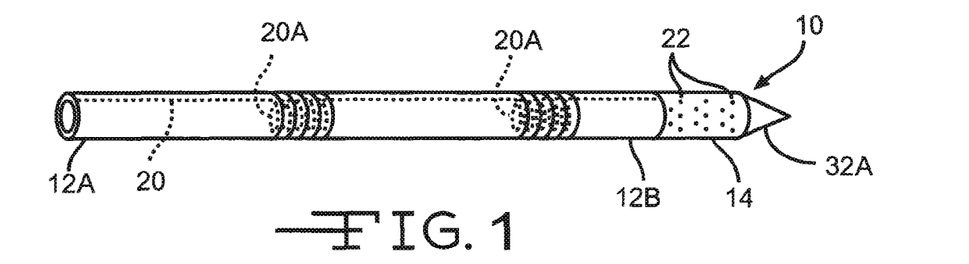
FIGS. 1 and 1A to 1C are schematics of a neural interface device 10 according to the present invention including a carrier 12, an electrical conductor 20, and a stylet 32.
Figure 1A:
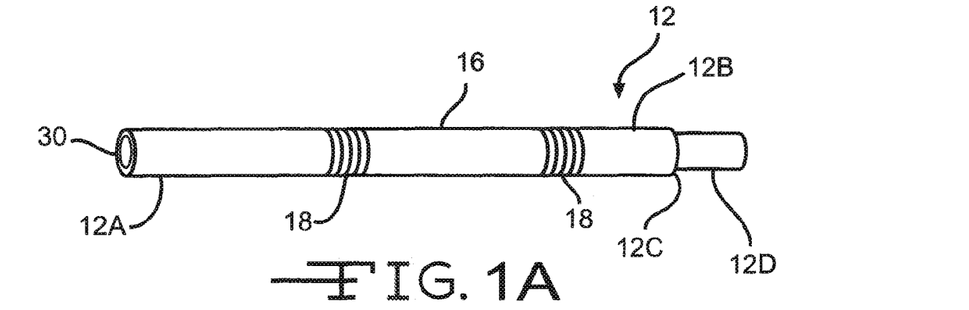
Figure 1B:
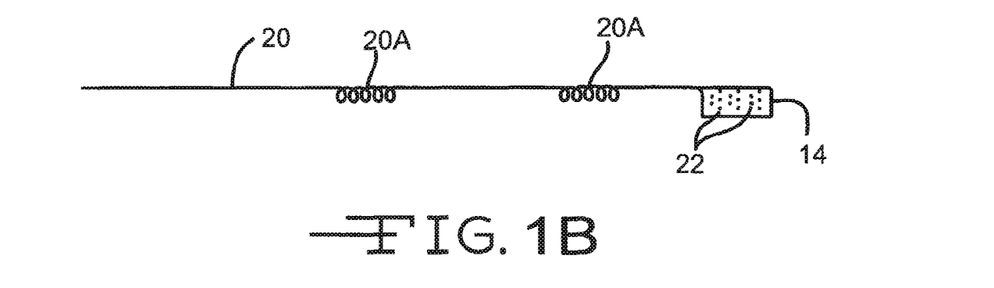
Figure 1C:
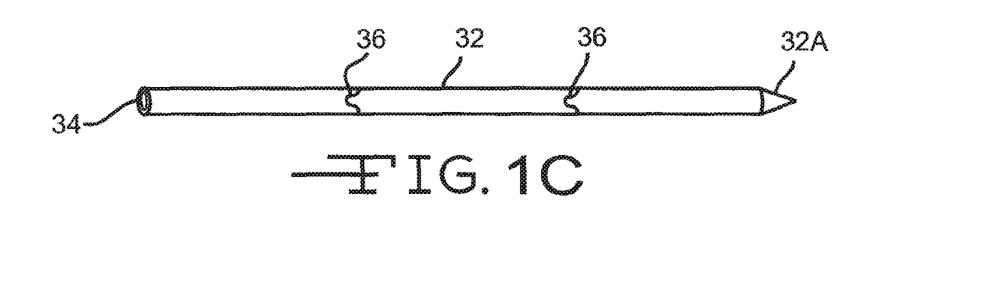
Figure 2:
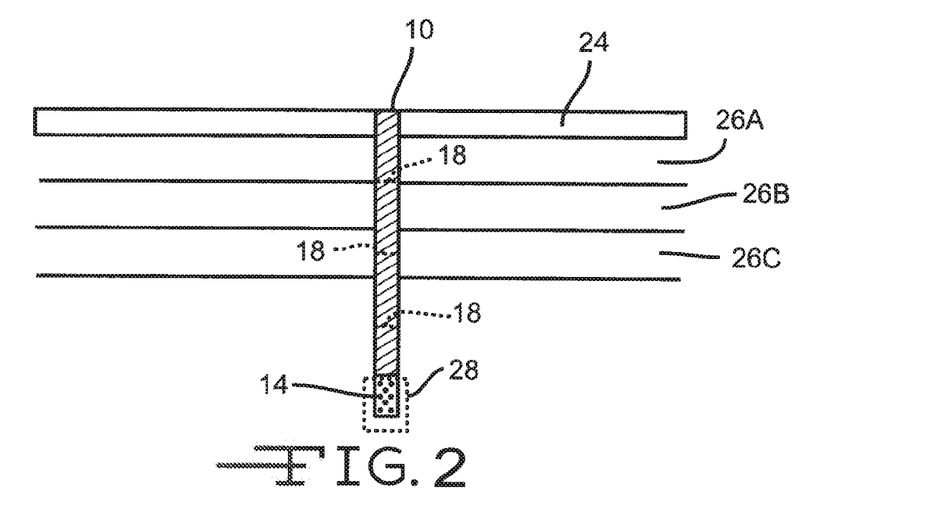
FIG. 2 is a schematic of the implanted neural interface device 10 having been implanted into body tissue.

FIG. 2 is a schematic illustration of the neural interface device 10 according to the present invention extending through the cranium 24 and into brain tissue. This drawing shows that brain tissue is not necessarily homogenous. For example, the brain tissue is depicted as comprising tissue layers or regions 26A, 26B and 260. The neural interface device 10 has been implanted into the brain tissue with the electrode array 14 residing at a target tissue site 28.

Figure 3:
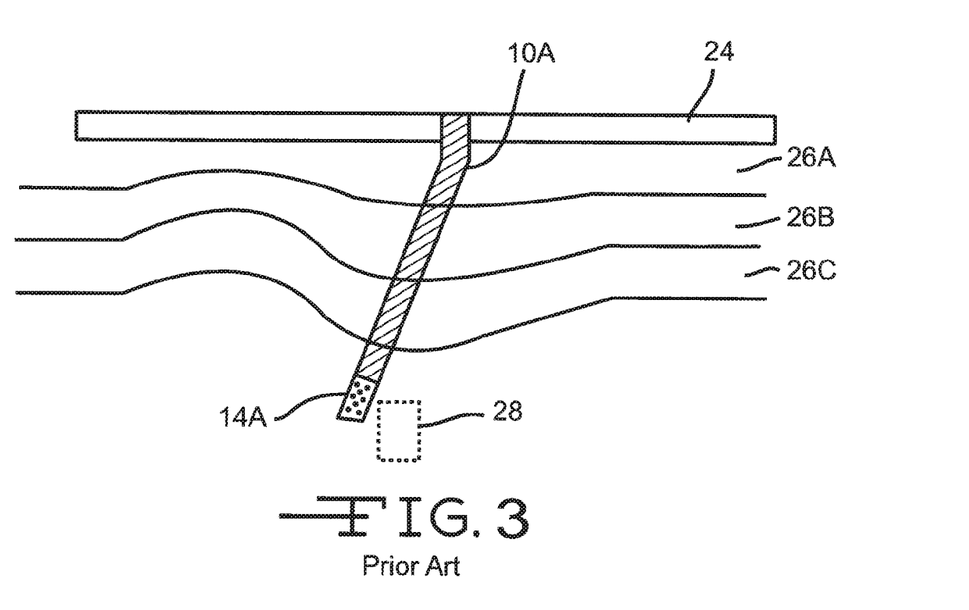
FIG. 3 is a schematic of a prior art neural interface device 10A after having been implanted in shifted body tissue.

Over time, regions of brain matter can become compressed or expanded through tissue changes. A tethered connection of the neural interface device to the cranium or other proximal structures may induce displacement as well. Such non-specific movement of body tissue can displace an implanted electrode array away from the targeted tissue 28. FIG. 3 shows that relative shifting has occurred between the various tissue layers or regions 26A, 26B and 260. This shifting results in the electrode array 14A of a prior art neural interface device 10A no longer residing at the target tissue site 28. The consequence can be diminished or even completely ineffective neural stimulation, which is undesirable.

The carrier 12 of the present neural interface device 10 is preferably at least partially made of a flexible material, such as an elastomer. Nitinol is another preferred material for the carrier 12. The carrier 12 is preferably tubular with a substantially cylindrical inner surface and includes one or more lumens 30 (FIG. 1A), such as for receiving a stylet 32 (FIG. 1C) therein. The stylet 32 has a pointed tip at its distal end 32A that helps facilitate insertion of the neural interface device 10 into tissue. If desired, the stylet 32 can have a lumen 34 for transporting fluids or serving as a passage for moving other devices (not shown) through the stylet/carrier assembly from the proximal carrier portion 12A to the distal carrier portion 12B and out the stylet end 32A thereof.

The stylet 32 may be adapted to remain in the tissue coupled to the carrier 12 and include deformable segments 36 similar to those 18 of the carrier 12 that enable compression and/or extension. If provided, the deformable segments 36 of the stylet 32 are preferably aligned with those of the carrier 12. That is so compression and extension of the stylet 32 and carrier 12 correspond to each other. Alternatively, the stylet 32 may be adapted for removal from the carrier 12 after implantation of the neural interface device 10 into body tissue.

FIGS. 4 and 4A to 4C illustrate a first embodiment of a carrier 12 according to the present invention. As previously described, the carrier 12 comprises the tubular sidewall 16 with a substantially cylindrical inner surface having one or more deformable segments 18 provided at spaced locations along its length. More specifically, the tubular sidewall 16 comprises a plurality of relatively less deformable carrier sidewall portions 16A, 16B, 16C, 16D and 16E, etc. spaced apart from each other by deformable segments 18. The less deformable sidewall portions 16A to 16E each have a first wall thickness that is substantially uniform around the annular extent thereof. This is illustrated in the cross-sections of FIGS. 4A and 4C.

Figure 4:
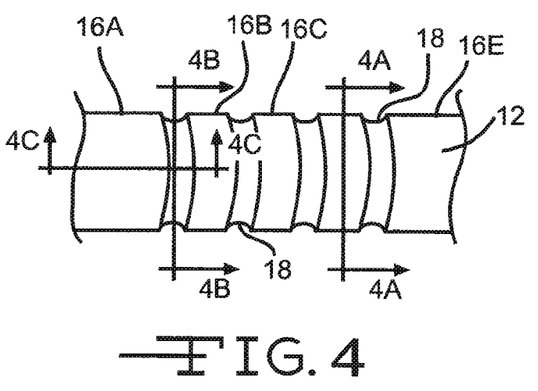
FIGS. 4 and 4A to 4C are schematics of a first embodiment of the carrier 12 for the neural interface device 10 including deformable segments 18.
Figure 4A:
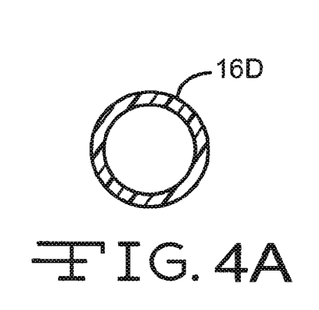
Figure 4B:
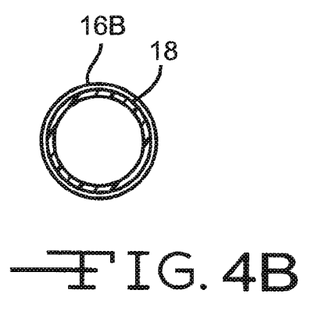
Figure 4C:
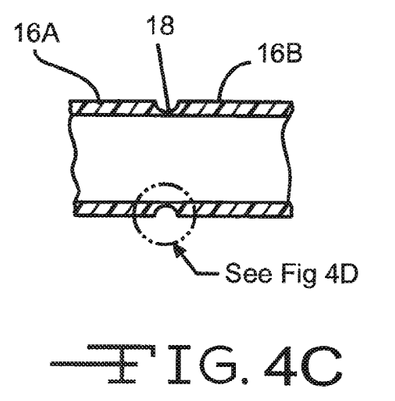
Figure 4D:
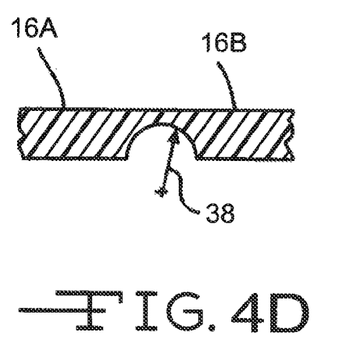
FIG. 4D is an enlarged view of the area indicted in FIG. 4C.

As shown in the cross-sections of FIGS. 4B and 4C, the deformable segments 18 are provided by an annular thinning of the wall thickness. As shown in FIG. 4D, the exemplary deformable segment 18 shown in FIG. 4C has a radiused curvature 38 from where it connects to proximal sidewall segment 16A and to distal sidewall segment 16B. That is the radiused. curvature of the deformable segment has a cross-section along a plane aligned along a longitudinal axis of the carrier 16 that meets the proximal carrier portion 16A of the first wall thickness and curves to a trough having a second wall thickness at about a mid-point to a distal carrier portion 16B of the first wall thickness. In other words, the carrier segments 16A to 16E, etc. generally have a first wall thickness and the deformable segments 18 generally have a second wall thickness that is less than the first wall thickness.

According to the first embodiment, the carrier 12 is of a continuous molded tubular construction with the thinned deformable segments 18 characterized as a mechanically thinning of the sidewall 16. Thinning of the sidewall can be done by any one of a number of methods including turning the carrier 12 on a lathe, by selective heat pressing the sidewall 16, and the like. Moreover, the carrier sidewall segments 16A to 16E and the deformable segments 18 can be separately manufactured and then serially connected together by thermal sealing, epoxy, or any suitable sealing or coupling method.

Figure 5A:
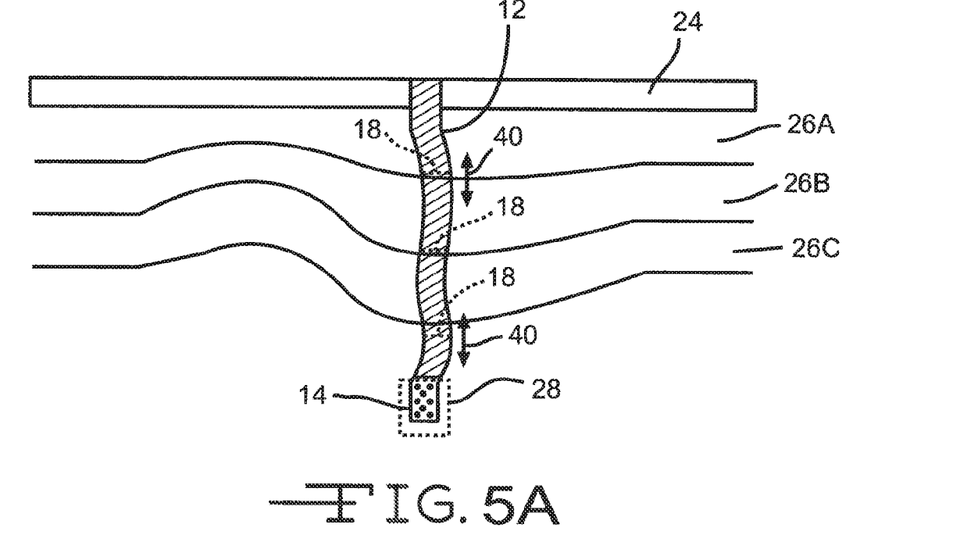
FIGS. 5A and 5B are schematics of the neural interface device 10 of the present invention after having been implanted in shifted body tissue.
Figure 5B:
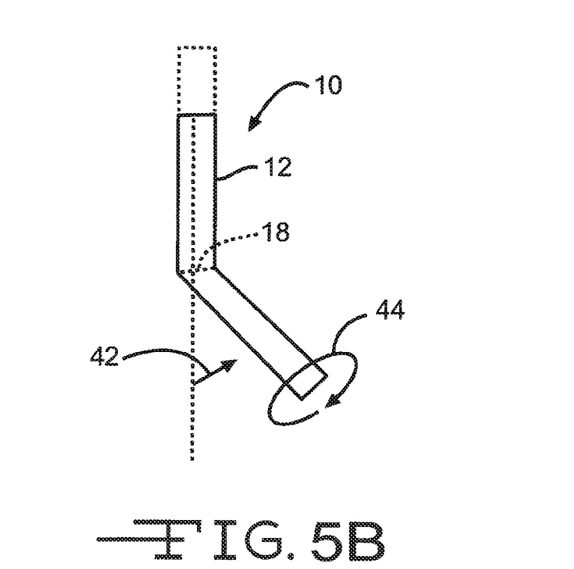

As shown in FIG. 5A, the deformable segments 18 enable the carrier 12 and the supported electrode array 14 to remain in the correct position and orientation with respect to the targeted tissue 28. The deformable segments 18 are more pliable than the remainder of the carrier sidewall 16 to preferably move in response to forces imparted on the carrier 12 and the electrode array 14 by the tissue. As shown in FIG. 5A, the deformable segments 18 enable the carrier 12 to move in compression and extension 40. FIG. 5B shows that the deformable segment 18 enables the carrier 12 to undergo both bending 42 and rotational 44 movement. As used herein, the term pliable in reference to the deformable segments 18 means easily bent, relatively more flexible, or relatively suppler.

Figure 6:
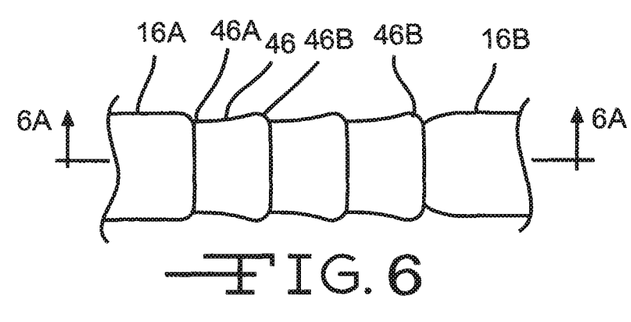
FIG. 6 is a schematic of another embodiment of tapered deformable segments 46 for the carrier 12 of an implantable neural interface device 10 according to the present invention.
Figure 6A:
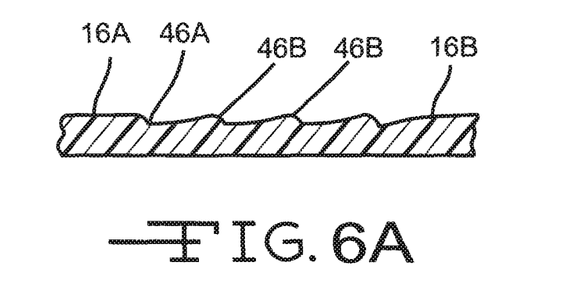
FIG. 6A is a cross-section along line 6A-6A of FIG. 6.

FIG. 6 illustrates that a deformable segment 46 does not necessarily require the radiused curvature 38 shown for deformable segment 18 in FIGS. 4C and 4D. Instead, the deformable segment 46 can have an irregular or graduated cross-sectional shape that is thinnest at a proximal end 46A and gradually thickens as the segment extends to a distal segment end 46B connected to the next carrier sidewall segment 16B. There can also be a number of deformable segments 46 connected end-to-end intermediate the carrier sidewall segments 16A and 16B. Moreover, the irregularly-shaped deformable segment 46 can be reversed to that shown in FIG. 6. That would be where the segment 46 is thickest at the proximal carrier sidewall segment 16A and thins as it extends to the next, more distal carrier sidewall segment 16B.

In another embodiment, the deformable segments 18 are made of a more flexible material or overall composite of materials having a lower elastic modulus than the carrier segments 16A to 16E, etc. For example, the carrier sidewall segments are of a polymeric material having a durometer ranging from about 75 A to about 60 A, more preferably of a polymeric material having a durometer ranging from about 70 A to about 55 A. Then, the deformable segments 18, 46 are of a more flexible polymeric material having a durometer ranging from about 50 A to about 25 A, more preferably from about 45 A to about 30 A.

In one embodiment, the carrier sidewall 16 is of a first polymeric material having a durometer ranging from about 75 A to about 60 A and the deformable segment 18 is of a second polymeric material having a durometer ranging from about 50 A to 25 A. Moreover, the carrier sidewall 16 of the first polymeric material and the deformable segment 18 of the second polymeric material have similar thicknesses.

Figure 7:
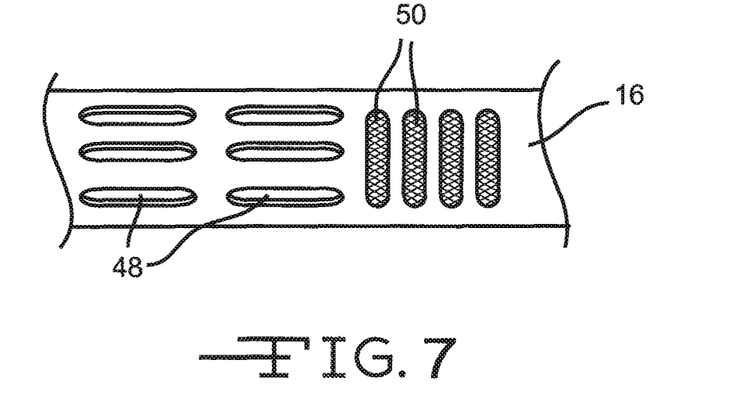
FIG. 7 is a schematic of anchoring features such as etched recesses 48 and through-holes 50 in the carrier sidewall 16.

In some embodiments, as shown in FIG. 7, the carrier may include one or more anchoring features, such as an etched recess 48 or a through-hole 50 in the carrier sidewall 16. The anchoring features 48, 50 may help promote tissue regrowth into the carrier structure, thereby improving anchoring of the carrier and/or first electrical subsystem in tissue. The carrier sidewall 16 may also be selectively coated with adhesion promoting factors, such as laminin, fibronectin, L1 molecule (Azemi, Cui 2011, Biomaterials), etc., to promote tissue adhesion.

The electrode array 14 is adapted to provide dynamic tunable electrical interaction with body tissue, and preferably includes a plurality of recording (e.g., sampling or mapping) and/or stimulation electrode sites. For example, the neural interface electrode array may be configured to provide stimulation ranging from macroscale specificity to microscale directional patterning.

Figure 8:
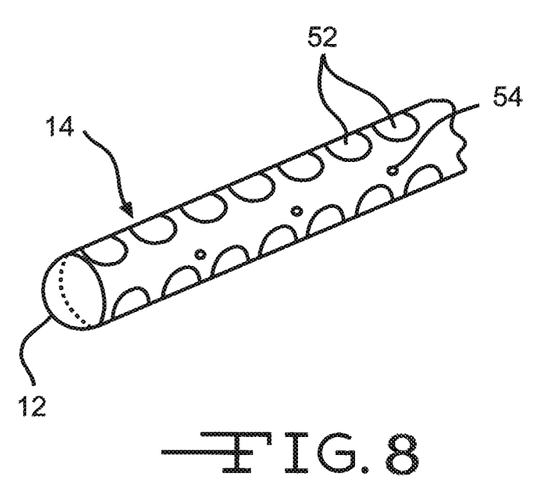
FIG. 8 is a schematic of an electrode array 14.

As shown in FIG. 8, one embodiment of the electrode array 14 includes sixty-four stimulation electrodes 52 and thirty-two recording electrodes 54 positioned axially along and circumferentially around the carrier 12. Each stimulation site 52 has a surface area of approximately 0.196 mm$^2$ (diameter approximately 500 µm), but may alternatively have any suitable surface area. Each recording site 54 has a surface area of approximately 0.00196 mm$^2$ (diameter approximately 50 µm), but may alternatively have any suitable surface area. The stimulation sites 52 are positioned such that four sites are equally distributed around the carrier circumference with a center-to-center spacing of approximately 750 µm, and distributed in 16 successive rows equally distributed along the longitudinal or axial direction of the carrier with a row-to-row spacing of approximately 750 µm. A pair of recording sites 54 is positioned on opposite sides of the carrier 12 between each row of stimulation sites 52. Each pair of recording sites 54 is rotated 90 degrees around the carrier with respect to an adjacent pair of recording sites. In alternative embodiments, the electrode array 14 may include any suitable number of stimulation electrode sites 52 and recording sites 54 arranged in any suitable manner.

In another embodiment, the electrode array 14 includes a plurality of cylindrical electrodes (not shown) spaced apart from each other axially along the length of the carrier 12. The cylindrical electrodes can be used in monopolar or bipolar modes to deliver approximately spherical potential fields from separate locations along the cylindrical carrier. Furthermore, although the carrier 12 is preferably a single tube, alternative embodiments may have any suitable shape, such as with branches or forks.

Figure 9A:
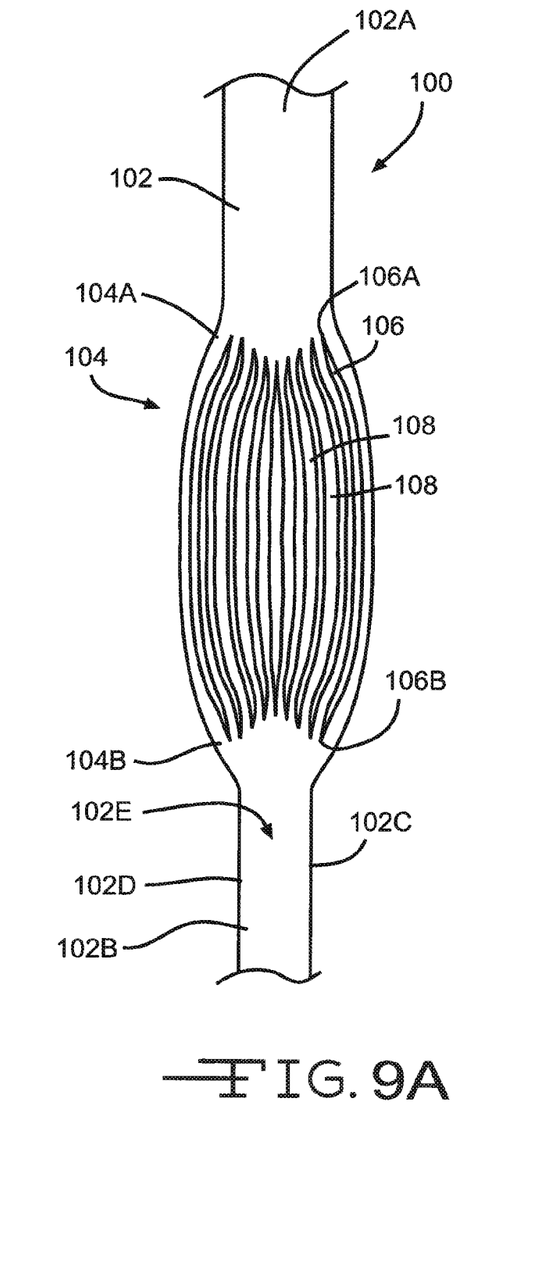
FIGS. 9A to 9B are schematics of another embodiment of a deformable connector 102 for a neural interface device 100 according to the present invention.
Figure 9B:
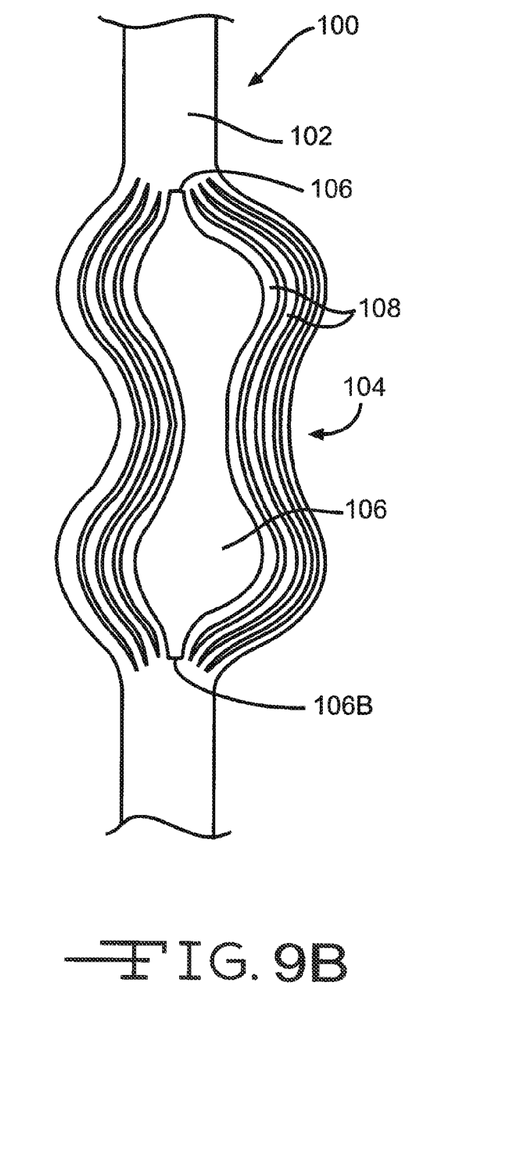
Figure 10A:
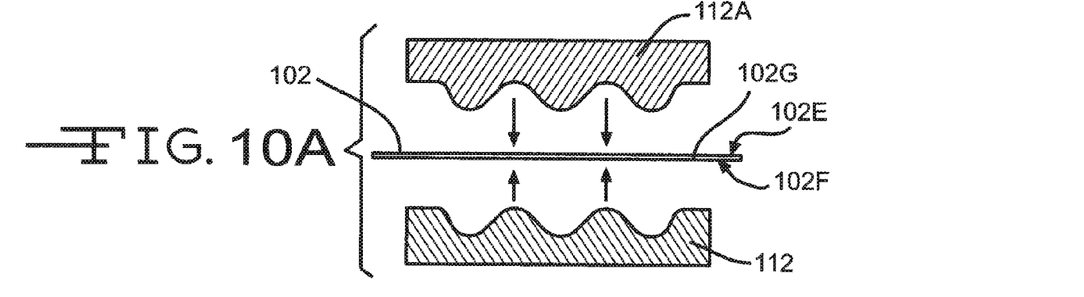
FIGS. 10A to 10D are schematics of a method of manufacturing the neural interface device 100 illustrated in FIGS. 9A and 9B.
Figure 10B:
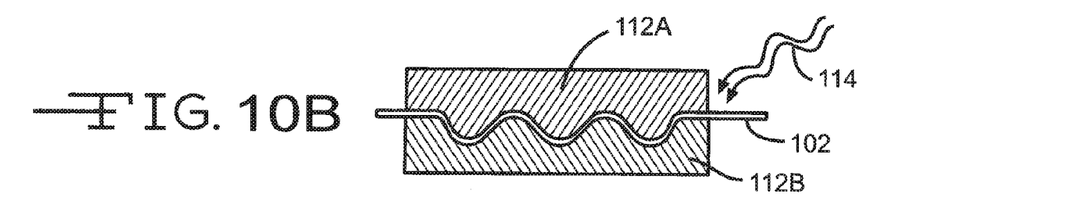
Figures 10C, 10D:
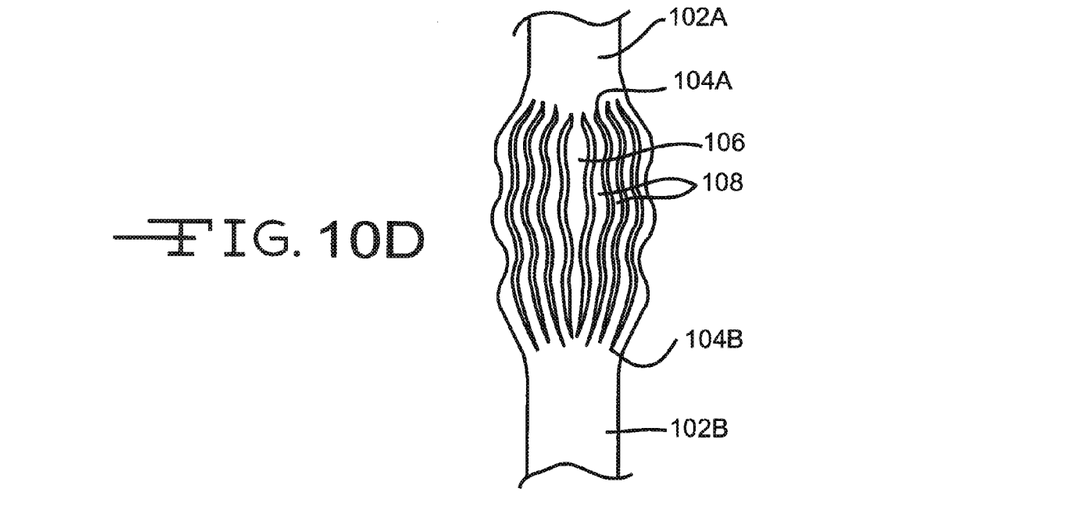

FIGS. 9 and 10 illustrate another preferred embodiment of a neural interface device 100 according to the present invention. The implantable neural interface device 100 comprises a flexible ribbon-type connector 102 having a length extending from a first, proximal connector end 102A to a second, distal connector end 102B, and a width extending between a third, right edge 102C and a fourth, left edge 102D. Further, the connector has a fifth, upper surface 102E spaced from a sixth, lower surface 102F by a thickness 102G (FIGS. 10A to 10C).

The ribbon-type connector 102 is preferably of a flexible polymer-based cable, such as of silicone or polyurethane, but may alternatively be any other suitable planar material. Preferably, the connector 102 is encased in silicone or another suitable biocompatible material.

The connector 102 includes at least one deformable segment 104 that functions in a similar manner as previously described with respect to the deformable segments 18, 46 of the carrier 12. The deformable segment 104 comprises at least one split 106 that extends from a proximal slitted end 106A to a distal slitted end 106B. The slit 106 is where the material of the ribbon-type connector 102 has been cut completely through its thickness 102G so that open space exists between adjacent strands 108 of the connector material. The slit 106 and, consequently, the open space extends from a proximal end 104A of the deformable segment to a distal end 104B thereof. More preferably, a plurality of slits 106 form a plurality of strands 108 along the length of the deformable segment 104. Each strand 108 is narrower and consequently more flexible than the unslit connector 102 and includes at least one conducting trace (not shown), and the like, extending from the first, proximal connector end 102A to the second, distal connector end 102B where the traces electrically connect to at least one electrode cite 22 of the previously described electrode array 14.

In this embodiment, the connector 102 with the deformable segment 104 may be fabricated using MEMS or a roll-to-roll technique, and a lithographic technique may be used to pattern the conductive traces. For instance, masking and etching techniques may be used to etch through specific regions of the planar connector 102 to form the one or more split 106. The number of splits 106 and their individual widths may be dependent on various factors, such as intended tissue anatomy of a specific application and manufacturing cost.

FIGS. 10A to 10D illustrate the connector 102 including the deformable segment 104 may include an undulating or three-dimensional shape 110. Undulations 110 facilitate an additional amount of linear expansion or contraction before the connector 102 reaches the tension or compression limits inherent in its material. The undulations 110 may be formed in both a slit and unslit portion. In that respect, the undulations 110 in the connector 102 may be formed by placing the planar structure connector 102 shown in FIG. 10A between complementary undulating top and bottom molds 112A and 112B, and applying heat 114 to anneal the structure. As shown in the side view of FIG. 10C and top plan view of FIG. 100, the thusly conditioned connector 102 has undulations 110 mirroring those of the molds 112A, 112B. Although FIGS. 10A to 10D primarily show undulations 110 along the axial direction of the connector 102, the connector may additionally and/or alternatively have undulations along the lateral direction or across the width extending from right edge 102C to left edge 102D thereof, or any suitable direction.

If desired, the planar connector 102 can be formed into a tubular shape.

The deformable segments 18, 46 of the neural interface device 10 and the deformable segment 104 of the neural interface device 100 preferably have lengths of from about 0.5 mm to about 2 mm. Moreover, when there is more than one of them in a neural interface device, they are spaced about 1 mm to about 5 mm from each other.

The proximal ends of the implantable neural interface devices 10, 100 are connectable to a second electrical subsystem (not shown) that functions to operate with the electrode array 14. For example, the second electrical subsystem may be a printed circuit board with or without on-board integrated circuits, comprise an on-chip circuitry for signal conditioning, filtering, or stimulus generation, be an Application Specific Integrated Circuit (ASIC), a multiplexer chip, a buffer amplifier, an electronics interface, an implantable pulse generator, an implantable rechargeable battery, integrated electronics for real-time signal processing of the commands sent to the stimulation electrodes 52 or received from the recording electrodes 54, integrated electronics for control of any fluidic components, and any other suitable electrical subsystem.

In one embodiment, the neural interface devices 10, 100 second may be coupled to a fixation point within the cranium of a patient. For example, a cranial chamber may be attached to the skull, preferably in a cranial burr hole, of a patient, and one or more of the neural interface devices 10, 100 may be coupled to the cranial chamber. One embodiment of such a cranial chamber may be similar to that described in U.S. Pat. No. 7,548,775, which is incorporated in its entirety by this reference. The neural interface devices 10, 100 may further include one or more fluidic channels that provide for delivery of a fluid (e.g., therapeutic drugs) to inhibit biologic response to the implant or to elicit a therapeutic response.

Some embodiments of the neural interface devices 10, 100 of the present invention may include any combination of any of them. One portion of a neural interface device may comprise features of neural interface device 10 while other portions may include features of the neural interface device 100. Moreover, the deformable segments 18, 46 and 104 may be regularly or irregularly spaced along the length of a neural interface device. For example, it may be desirable to impart greater flexibility to selected regions of the carrier, such as spacing the deformable segments progressively closer together towards a distal end or a proximal end of the carrier. Some of the deformable segments may additionally and/or alternatively be more easily deformed than other deformable segments, which may further provide greater flexibility to selected regions of the neural interface device.

A person skilled in the art will recognize from the previous detailed description including the drawing figures, that modifications and changes can be made to the preferred embodiments of the present invention without departing from the scope of the invention defined in the following claims.

What is claimed is:

1. A neural interface device, which comprises:
   a) a carrier, comprising:
      i) a carrier sidewall having a length extending from a proximal carrier end of a proximal carrier portion to a distal carrier portion having a distal carrier end,
      ii) wherein the carrier sidewall extends to spaced apart first and second major surfaces and has a width extending from a third carrier edge to an opposed fourth carrier edge, the first and second major surfaces meeting the proximal and distal ends and the third and fourth edges, and
      iii) wherein the proximal carrier portion has a first thickness between the first and second major surfaces and extending to an intermediate step delineating the distal carrier portion, and wherein the distal carrier portion has a second thickness between the first and second major surfaces that is less than the first thickness;
   b) a substrate supported on the distal carrier portion abutting the step;
   c) at least one electrode supported on the substrate, wherein the electrode is configured for at least one of electrical stimulation of body tissue and sensing of physiological characteristics of the body tissue;
   d) an electrical conductor that extends from the proximal carrier portion to electrically connect to the at least one electrode, wherein a proximal end of the electrical conductor is electrically connectable to a medical device; and
   e) at least one deformable segment of the proximal carrier portion intermediate the proximal carrier end and the step, wherein the deformable segment comprises at least one slit extending completely through the first thickness, and wherein the at least one slit provides an open slit space having an open slit length extending from a proximal slit end spaced distally from the proximal carrier end to a distal slit end spaced proximally from the distal carrier end to thereby provide first and second strand portions of the carrier sidewall, the first and second strand portions being intermediate the proximal and distal carrier ends and the third and fourth carrier edges.

2. The neural interface device of claim 1 wherein there is a plurality of slits, each slit having an open slit length of a depth that extends completely through the carrier thickness, part way along the first length of the carrier sidewall intermediate the proximal and distal carrier ends and the third and fourth carrier edges.

3. The neural interface device of claim 2 wherein the carrier sidewall has a tubular shape with the third and fourth carrier edges meeting each other, and wherein the plurality of slits are provided at spaced location around an annular extent of the tubular carrier sidewall.

4. The neural interface device of claim 1 wherein the first and second strand portions each have a first undulating shape.

5. The neural interface device of claim 4 wherein a second segment of the carrier sidewall that is not provided with a slit has a second undulating shape.

6. The neural interface device of claim 5 wherein the second undulating shape extends along at least one of an axial direction along the length of the carrier and a lateral direction along the width of the carrier.

7. The neural interface device of claim 1 wherein the carrier is of a polymeric material.

8. The neural interface device of claim 1 wherein the carrier has a planar structure that is rollable into a tubular shape.

9. The neural interface device of claim 1 wherein there are at least two deformable segments provided by respective slits at spaced locations along the length of the carrier.

10. The neural interface device of claim 1 wherein the electrical conductor is relatively more stretchable at a location coinciding with the deformable segment of the carrier.

11. The neural interface device of claim 1 wherein the carrier sidewall has a substantially cylindrical inner surface provided by one of the first and second major carrier surfaces.

12. The neural interface device of claim 1 wherein the substrate is of a polymeric material selected from the group consisting of parylene, polyimide, silicone, and mixtures thereof.

13. The neural interface device of claim 1 wherein the deformable segment is compressible, tensile, articulatable, and rotatable.

14. The neural interface device of claim 1 wherein a first undulating shape extends along at least one of an axial direction along the length of the carrier and a lateral direction along the width of the carrier.

15. The neural interface device of claim 1 wherein the substrate comprises perforations that permits the carrier to anchor therein.

16. A neural interface device, which comprises:
   a) a carrier, comprising:
      i) a carrier sidewall having a length extending from a proximal carrier end of a proximal carrier portion to a distal carrier portion having a distal carrier end, ii) wherein the carrier sidewall extends to spaced apart first and second major surfaces and has a width extending from a third carrier edge to an opposed fourth carrier edge, the first and second major surfaces meeting the proximal and distal ends and the third and fourth edges, and iii) wherein the proximal carrier portion has a first thickness between the first and second major surfaces extending to an intermediate step delineating the distal carrier portion, and wherein the distal carrier portion has a second thickness between the first and second major surfaces that is less than the first thickness;

b) a substrate supported on the distal carrier portion;

c) at least two electrodes supported on the substrate, wherein a first one of the electrodes is configured for electrical stimulation of body tissue and a second one of the electrodes is configured for sensing of physiological characteristics of the body tissue;

d) at least two electrical conductors extending from the proximal carrier portion to electrically connect to a respective one of the first, electrical stimulation electrode and the second, sensing electrode, wherein proximal ends of the electrical conductors are electrically connectable to a medical device; and e) at least one deformable segment of the proximal carrier portion intermediate the proximal carrier end and the step, wherein the deformable segment comprises at least one slit extending completely through the first thickness, and wherein the at least one slit provides an open slit space having an open slit length extending from a proximal slit end spaced distally from the proximal carrier end to a distal slit end spaced proximally from the distal carrier end to thereby provide first and second strand portions of the carrier sidewall, the first and second strand portions being intermediate the proximal and distal carrier ends and the third and fourth carrier edges, f) wherein the first strand portion supports the first electrical conductor and the second strand portion supports the second electrical conductor.

17. The neural interface device of claim 16 wherein there is a plurality of electrodes comprising electrical stimulation electrodes and sensing electrodes and a plurality of strand portions supporting an electrical conductor electrically connected to a respective one of the electrodes.

18. The neural interface device of claim 17 wherein deformable segment comprising the plurality of strand portions has a first undulating shape that extends along at least one of an axial direction along the length of the carrier and a lateral direction along the width of the carrier, and wherein a second segment of the carrier sidewall that in not provided with a slit has a second undulating shape that extends along at least one of the axial and lateral directions of the carrier.

19. A neural interface device, which comprises:

a) a carrier, comprising:

i) a carrier sidewall having a length extending from a proximal carrier end of a proximal carrier portion to a distal carrier portion having a distal carrier end, ii) wherein the carrier sidewall extends to spaced apart first and second major surfaces and has a width extending from a third carrier edge to an opposed fourth carrier edge, the first and second major surfaces meeting the proximal and distal ends and the first and second edges, and iii) wherein the proximal carrier portion has a first thickness between the first and second major surfaces and extending to an intermediate step delineating the distal carrier portion, and wherein the distal carrier portion has a second thickness between the first and second major surfaces that is less than the first thickness;

b) a substrate supported on the distal carrier portion;

c) a plurality of electrodes supported on the substrate, wherein the plurality of electrodes comprise electrical stimulation electrodes configured for electrical stimulation of body tissue and sensing electrodes configured for sensing of physiological characteristics of the body tissue;

d) a plurality of electrical conductors extending from the proximal carrier portion to electrically connect to either one of the electrical stimulation electrode or one of the sensing electrodes, wherein proximal ends of the electrical conductor are electrically connectable to a medical device; and e) at least one deformable segment of the proximal carrier portion intermediate the proximal carrier end and the step, wherein the deformable segment comprises a plurality of slits extending completely through the first thickness, and wherein each of the plurality of slits provides an open slit space having an open slit length extending from a proximal slit end spaced distally from the proximal carrier end to a distal slit end spaced proximally from the distal carrier end to thereby provide respective first and second strand portions of the carrier sidewall, the first and second strand portions provided by each slit being intermediate the proximal and distal carrier ends and the third and fourth carrier edges, f) wherein each one of the plurality of strand portions supports at least one electrical conductor electrically connected to either an electrical stimulation electrode or a sensing electrode, g) wherein each of the plurality of strand portions has a first undulating shape, and h) wherein a second segment of the carrier sidewall that in not provided with a slit has a second undulating shape.

20. The neural interface device of claim 19 wherein the first undulating shape extends along at least one of an axial direction along the length of the carrier and a lateral direction along the width of the carrier, and wherein the second undulating shape extends along at least one of the axial and lateral directions of the carrier.

\* \* \* \* \*